US007273625B2

(12) United States Patent
Lee

(10) Patent No.: US 7,273,625 B2
(45) Date of Patent: Sep. 25, 2007

(54) MINARI EXTRACT FOR PREVENTING THE INDUCTION AND METASTASIS OF CANCER BY CARCINOGENS CONTAINED IN CIGARETTE SMOKE, FERMENTED FOODS OR ALCOHOLIC DRINKS

(76) Inventor: Insu P. Lee, Tri-Life Research, Inc. P.O. Box 34592, West-Bethesda, MD (US) 20827

( * ) Notice: Subject to any disclaimer, the term of this patent is extended or adjusted under 35 U.S.C. 154(b) by 0 days.

(21) Appl. No.: 10/258,090

(22) PCT Filed: Dec. 20, 2000

(86) PCT No.: PCT/JP00/09060

§ 371 (c)(1),
(2), (4) Date: Oct. 18, 2002

(87) PCT Pub. No.: WO01/80869

PCT Pub. Date: Nov. 1, 2001

(65) Prior Publication Data
US 2003/0104089 A1 Jun. 5, 2003

(30) Foreign Application Priority Data
Apr. 21, 2000 (KR) .............................. 2000-21271

(51) Int. Cl.
*A01N 65/00* (2006.01)
(52) U.S. Cl. ..................................................... 424/725
(58) Field of Classification Search ................ 424/725; 425/725
See application file for complete search history.

(56) References Cited

FOREIGN PATENT DOCUMENTS

JP          02-101013         12/1990

OTHER PUBLICATIONS

Park J C et al., Planta Medica (1996), 62(6): 488-490. Protective effect of *Oenanthe javanica* on the hepatic lipid peroxidation in bromobenzene-treated rats and its bioactive component.*
Park J C et al., Phytotherapy Research (1997), 11(3): 260-262. Effects of methanol extract of *Oenanthe javanica* on the hepatic alcohol-metabolizing enzyme and its bioactive compound.*
Harborne J B et al., J of Chromatography (1984), 299(2): 377-386. Use of high-performance liquid chromatography in the separation of flavonl glycosides and flavonol sulfates.*
Vincieri F F et al., International J of pharmaceutics (1988), 48(1-3): 119-124. Stabilization of tinctures with cyclodextrins: a tincture from the fruits of *Oenanthe aquatica* L.*
Tatsuta H et al., Sci. Repts. Tohoku Univ., First Ser. (1956), 39: 243-5. Studies on water soluble flavonoids. III. Extraction of persicarin from *Oenanthe stolonifera*.*
Matsushita et al., Nippon Nogei Kagaku Kaishi (1965), 39(8): 317-318. Flavonoid constituents of the flowers of *Oenanthe stolinifera*: rutin, persicarin, and quercitin.*

Lijun B et al., Shipin Kexue (Beijing), 1999, 20(12): 35-37. Optimum conditions for extraction of flavonoids from *Oenanthe javanica*.*
Sato T et al., Yakugaku Zasshi, 1977, 97(6): 698-700. Studies on the components of *Oenanthe-javanica*. Part 3: On the etheral extract and others. Abstract.*
Park J C et al., Phytotherapy Research, 1997, 11(3): 260-262. Effects of methanol extract of *Oenanther javanica* on the hepatic alcohol-metabolizing enzyme system and its bioactive component. Abstract.*
Tatsuta H et al., Nippon Kagaku Kaishi, 1954, Pure Chem. Sect 75, pp. 941-942. Isolation of persicarin from *Oenanthe stolonifera* DC. Abstract.*
Matsushita A et al., Nippon Nogei Kagaku Kaishi, 1965, 39(8): 317-318. Flavonoid constituents of the flowers of *Oenanthe stolinifera*: rutin, persicarin, and quercetin. Abstract.*
D.J. Mabberley, The Plant Book, Second Edition, 1997. Cambridge University Press, The United Kingdom, pp. 46, 47, 736 and 737.*
Kwang Hyuk Kim, et al., Effects of Linoleic acid, Ursolic acid, Phytol, and Small water dropwort Extract on the Phagocyte of Mice, *Environimental mutagens & Carcinogens*, 13-2:135-144 (1993).
Kwang Hyuk Kim, et al., Effects of Small Water Dropwart Extract on Cellular Immune Response of Mice, *J. Korean Soc. Microbiol.*, vol. 28, No. 5, 1993.
Jong Cheol Park, et al., Isorhamnetin Sulphate from the Leaves and Stems of *Oenanthe javanica* in Korea, *Planta med. 61*, (1995) 377-378.
Christian Malaveille, et al., Antimutagenic dietary phenolics as antigenotoxic substances in urothelium of smokers, *Mutation Research 402*, (1998) 219-224.
Christian Malaveille, et al., Dietary phenolics as anti-mutagens and inhibitors of tobacco-related DNA adduction in the urothelium of smokers, *Carcinogenesis*, vol. 17, No. 10, pp. 2193-2200, 1996.
Jong-Cheol Park, et al., Anti-Inflammatory and Analgesic Effects of the Components from Some Edible Plants, *J. Korean Soc. Food Nutr.*, 23 (4), 671-674 (1994).
Jong-Cheol Park, et al., Studies on the Chemical Components and Biological Activities of Edible Plants in Korea (VI), *J. Korean Soc. Food Nutr.*, 23 (1), 116-119 (1994).
Murakami et al., "Screening for in vitro anti-tumor-promoting activities of edible plants from Indonesia", *Cancer Detect Prev.*, 1998:22(6): Abstract only.
Fujioka et al., "Antiproliferative constituents from umbelliferae plants. V. A new furanocoumarin and falcarindiol furanocoumarin ethers from the root of Angelica japonica", *Chem. Pharm. Bull (Tokyo)*, Jan. 1999; 47(I): Abstract only.
Craig, WJ, "Health-promoting properties of common herbs", *Am. J. Clin. Nutr.*, Sep. 1999:70(3 Suppl): Abstract only.

(Continued)

*Primary Examiner*—Michele Flood
(74) *Attorney, Agent, or Firm*—Fay Sharpe LLP

(57) ABSTRACT

An extract of the Minari plant containing a component which prevents cancer and cancer metastasis. A Minari extract which is useful for the prevention of cancer and cancer metastasis induced by urethane (EC (ethylcarbamate)), which is a carcinogen present in fermented foods or alcoholic beverages, or by NNK[{(4-N-methyl-N-nitrosoamino)-1-(3-pyridyl)-1-buta none)}], which is a carcinogen present in cigarette smoke.

6 Claims, 7 Drawing Sheets

OTHER PUBLICATIONS

Ito et al., "Relationship between serum xanthophylis levels and the consumption of cigarettes, alcohol or foods in healthy inhabitants of Japan", *Int. J. Epidemiol.*, Sep. 1991: Abstract only.

Kobayashi et al., "Cationic chlorophyll derivatives with SOD, mimicking activity suppress the proliferation of human ovarian cancer cells", *Cancer Biother. Radiopharm.*, Abstract only.

Lubet et al., "chemopreventive efficacy of anethole trithione, N-acetyl-L-cysteine, miconazole and phenethylisothiocyanate in the DMBA-induced rat mammary cancer model", *Int. J. Cancer*, Jul. 3, 1997; Abstract only.

Uedo et al., "Inhibition by D0-limonene of gastric carcinogens induced by N-methyl-N'-nitro-N-nitrosoguanidine in Wistar rats", *Cancer Lett.*, Apr. 1, 1999; 137(2): 131-6, Abstract only.

Mahmoud et al., "Plant phenolics decrease intestinal tumors in an animal model of familial adenomatous polyposis", *Carcinogenesis*, 2000 Abstract only.

* cited by examiner

Prevention by Minari extract of lung cancer induced by NNK

Minari concentration (% feed, w/w)

NNK (4 mg/mouse)

\* Lung cancer incidence rate was significantly lower in the Minari groups than in the control group ($p < 0.05$)

Suppression by Minari extract of Cyclin D1 oncogene expression which is activated by NNK

* There is a significant difference between the control group and the Minari group ($p < 0.05$)

MINARI EXTRACT FOR PREVENTING THE INDUCTION AND METASTASIS OF CANCER BY CARCINOGENS CONTAINED IN CIGARETTE SMOKE, FERMENTED FOODS OR ALCOHOLIC DRINKS

TECHNICAL FIELD

The present invention relates to an extract of the Minari plant containing a component which prevents cancer and cancer metastasis. More particularly, the present invention relates to a Minari extract which is useful for the prevention of cancer and cancer metastasis induced by urethane (EC (ethylcarbamate)), which is a carcinogen present in fermented foods or alcoholic beverages, or by NNK[{(4-N-methyl-N-nitrosoamino)-1-(3-pyridyl)-1-buta none}], which is a carcinogen present in cigarette smoke.

BACKGROUND ART

Urethane and NNK are known to be involved in the occurrence of various types of cancer.

Urethane causes lung cancer and liver cancer in mice in a dose-dependent manner. The virtually safe dose (VSD) of urethane in humans has been calculated to be $1.8 \times 10^{-4}$ mg/kg body weight for lung cancer and $7.2 \times 10^{-5}$ mg/kg body weight for liver cancer (K. Inai et al., Jpn. J. Cancer Res. 82, pp. 380-385, April 1991).

The offspring of pregnant mice, treated with urethane during gestation and lactation, had a significantly increased incidence of embryonic tumors, lung cancer, and ovarian cystadenomas via placental transmission, as well as endometrial hyperplasias and uterine hemangiomas in the pregnant parent mice (T. Nomura, Cancer Research, 33, pp. 1677-1683, 1973, July).

When administered per os, urethane causes lung cancer, lymphomas, hepatoma, stomach papillomas, sebaceous carcinomas, mammary tumors, squamous-cell tumors, leukemia, and mesenchymal tumors in mice (IARC MONOGRAPHS ON THE EVALUATION OF THE CARCINOGENIC RISK OF CHEMICALS TO MAN, vol. 7, pp. 111-131, the views of two IARC Working Groups on the Evaluation of the Carcinogenic Risk of Chemicals to Man which met in Lyon, 4-11 Feb. 1974 and 18-24 Jun. 1974).

Moreover, regulatory limits are implemented on urethane in Canada because urethane is produced through alcoholic fermentation and is contained at a certain level in brews such as wine (Ethyl Carbamate in Alcoholic Beverages and Fermented Foods, ACS Symposium Series No. 484, Food Safety Assessment, ed. by John W. Finley et al., pp. 419-428, published in 1992 by American Chemical Society; Identification of Volatile Constituents from Grapes, J. Agric. Food Chem., vol. 24, no. 2, pp. 329-331, 1976; RATIONALE FOR THE ESTABLISHMENT OF GUIDELINES TO LIMIT ETHYL CARBAMATE LEVELS IN ALCOHOLIC BEVERAGES, BUREAU OF CHEMICAL SAFETY, FOOD DIRECTORATE HEALTH PROTECTION BRANCH, HEALTH & WELFARE CANADA, pp. 1-8; Ethylcarbamate in Fermented Beverages and Foods, Cornelius S. Ough, J. Agric. Food Chem. vol. 24, no. 2, pp. 323-327).

NNK is a potential carcinogen present in cigarette smoke (Djordijevic, M. V. et al., A comparison of selected components in the mainstream smoke of the leading U.S. and Japanese cigarettes. In: Proceedings of the CORESTA smoke and Technology Meeting, pp. 200-217, Nov. 3-8, 1996).

Among other types of cancer, the incidence of lung cancer has continued to increase in both men and women. The occurrence of lung cancer is significantly related to smoking and alcohol consumption. The International Agency for Research on Cancer has indicated synergistic consumption of smoking and alcohols, suggesting that NNK and urethane which have been totally taken in through smoking and through intake of alcoholic beverages are a cause for lung cancer. It has been indicated that smoking directly contributes to 45% of cancer deaths in men and 21.5% in women. It appears that death from lung cancer has replaced cardiac diseases as a main cause of death among smokers in the United States.

There is a need for a dietary ingredient for preventing carcinogenesis due to smoking and alcohol intake.

DISCLOSURE OF THE INVENTION

The present invention relates to a dietary ingredient of Minari extract for preventing occurrence and subsequent metastasis of cancer.

Minari, a plant of Family Umbelliferae, is grown and cultivated in damp soil or in rice paddies, and traditionally known as a detoxifying agent. It is known to very effectively detoxify alcohol toxicity by promoting excretion of alcohol.

In Chinese herbal medicine, Minari is used to treat jaundice, gastrointestinal diseases, neurosis, and obesity. However, it has not previously been found that Minari prevents occurrence of cancer and even obstructs metastasis of cancer. The inventor has found that a dietary ingredient of Minari extract obstructs activation of potential precarcinogens, eliminates potential free radicals which are produced through metabolism of carcinogens, and directly eliminates free radical generators among chemical carcinogens, and therefore that the Minari extract is highly effective for cancer prevention. Thus, the present invention was accomplished.

The present invention provides a Minari extract containing a component(s) which prevents cancer and cancer metastasis.

According to one aspect of the present invention, the extract is prepared by solvent extraction. According to another aspect of the present invention, the extract is prepared by extraction in hot water.

According to another aspect of the present invention, the composition is selected from the group consisting of persicarin, hyperoside, rutin, quercetin, chlorophyll, xanthophyll, isohamenetin, phenethylisothiocyanate, phenalkylisothiocyanate, flavons, flavonols, and d-limonene.

According to still another aspect of the present invention, the cancer is cancer which can be induced by urethane or NNK[{(4-N-methyl-N-nitrosoamino)-1-(3-pyridyl)-1-buta none}]. According to a further aspect of the present invention, the cancer is lung cancer or cancer via placental transmission or embryonic tumors.

The present invention further provides a composition which prevents cancer and cancer metastasis containing a Minari extract and a pharmaceutically acceptable carrier.

According to one aspect of the present invention, the composition is in a form selected from the group consisting of powder, liquid, tablets, capsules, and pellets.

BEST MODES FOR CARRYING OUT THE INVENTION

Figure 1:
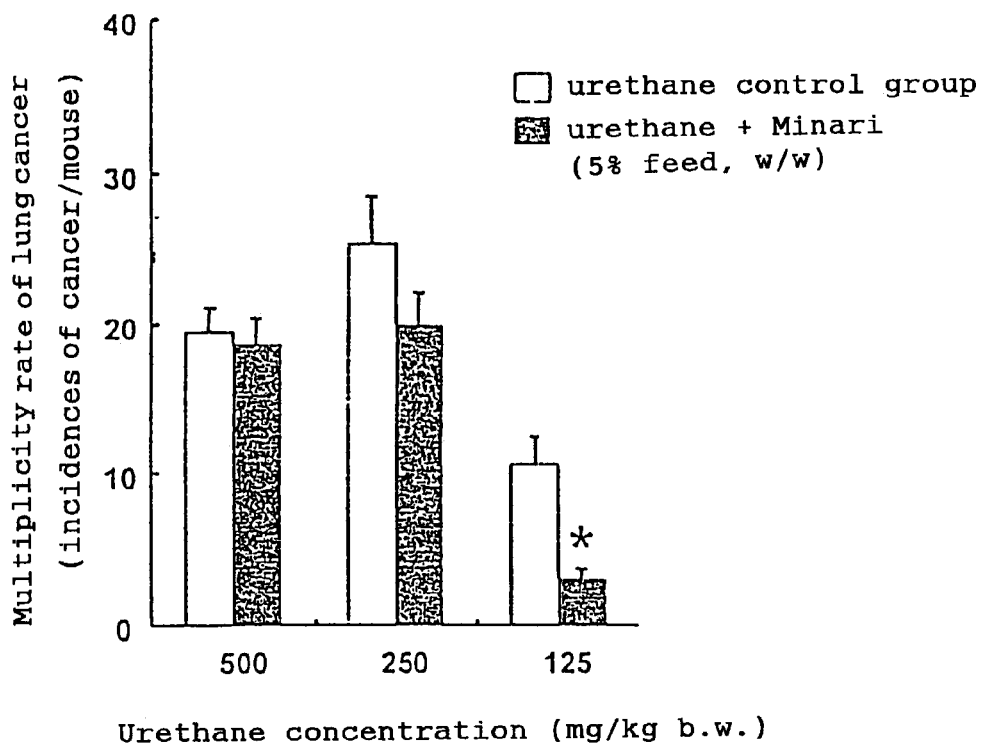
FIG. 1 demonstrates different levels of lung cancer multiplicity induced in three experimental groups of A/J mice, taken after 4 months following a single gavage of different amounts of urethane, as well as the suppressive effects of the Minari extract. Each of the three experimental groups, which respectively received a single administration of a 125, 250, or 500 mg/kg dose of urethane, was divided into two subgroups: one of the subgroups received a normal feed (urethane control group), while the other subgroup was allowed to take, ad lib., a feed to which Minari extract was added at a 5% concentration (w/w) for 4 months (urethane+Minari). After the experiment, the multiplicity rate of lung cancer (incidences of cancer/mouse) was observed for each group.

The term "Minari" as used in the present invention refers to a plant belonging to Family Apiaceae (Umbelliferae), and typically a Korean native dol-minari of Genus Oenanthe.

The term "Minari extract" refers to a liquid obtained through extraction from a Minari plant (leaves, stem, and roots) using below-described extraction solvents, usually deionized water, as well as a solid including powder obtained by lyophilizing the same.

A Minari extract can be prepared by a method which is widely used in common. For example, Minari is washed, dried, and pulverized first. Then, extraction is carried out by using various solvents. In general, the extraction solvent is added in a 2 to 10× weight to the Minari powder. Examples of extraction solvents include water, ethanol, propanol, butanol, acetone, 1,3-butylene glycol, ethyl acetate, hexane, methylene chloride, methanol, or ethyl acetate. Typically, water is used to prepare a Minari extract. A mixture of two or more kinds among the aforementioned solvents may be used.

Typically, a mixture of Minari extract and a solvent is subjected to extraction with agitation using a magnetic stirrer or the like at room temperature for 24 hours. For example, by using deionized water, extraction is carried out for 24 consecutive hours at 70° C. Thereafter, the deionized water is separated, followed by lyophilization. The lyophilized powder is used as Minari extract. The components contained in the Minari extract prepared in the above manner may be separated by a HPLC (high performance liquid chromatography), which is well-known to the those skilled in the art, and the separated components may be identified by an NMR technique (nuclear magnetic resonance technique).

The inventor has confirmed through NMR spectroscopy that persicarin, hyperoside, rutin, quercetin, chlorophyll, xanthophyll, isohamenetin, phenalkylisothiocyanate, phenethylisothiocyanate, flavons, flavonols, and d-limonene are contained in the Minari extract thus prepared.

Some of these natural substances are known as antioxidants, and these components are considered to act in a synergistic manner to prevent carcinogenesis. Accordingly, a Minari extract containing these components can capture various free radicals such as superoxides and hydroxy free radicals, thereby preventing lung cancer and metastatic tumors induced by NNK (a potential carcinogen among other carcinogenic chemicals such as polyaromatic hydrocarbons, aza-arenes, aromatic amine, conjugated alkylaldehyde, formaldehyde, NO, urethane, and nicotine ornitrosamine, etc.),urethane (ethyl carbamate or alkyl carbamate in fermented foods and alcoholic beverages), or the like. Alternatively, these components can obstruct the expression of various oncogenes.

The Minari extract may be used alone or in combination with Ostericum coreanum.

The Minari extract can be used as dried powder, an additive to foods, or a drink, and in formulations such as capsules, tablets, or pellets fabricated by using a common binder. The detailed methodology concerning the present invention will be described in the examples below, which are not intended to limit the scope of claims.

The present invention is based on work directed to therapies using Minari extract in various dosage forms, against, for example, a carcinogen present in fermented foods or alcoholic beverages and/or a potential carcinogen(s) present in cigarette smoke. However, the inventor and the applicant contemplate that the present invention can be applied to other types of cancer and metastatic cancer (including cancer caused by other carcinogens). Furthermore, experimental schemes and its protocols can be altered for practice.

The effects of preventing cancer and cancer metastasis provided by the Minari extract of the present invention can be confirmed by examining whether or not diets containing Minari extract at various concentrations affect the expression level of the cyclin D1 gene in the lung tissue of mice which have been treated with urethane. The effects of preventing cancer and cancer metastasis provided by the Minari extract of the present invention can be confirmed by examining whether or not diets containing Minari extract at various concentrations affect the expression level of PCNA (proliferative cell nuclear antigen) in the lung tissue of mice which have been treated with carcinogenic urethane.

Furthermore, the effects of preventing cancer and cancer metastasis provided by the Minari extract of the present invention can be confirmed by examining to what extent the oxidative damage to DNA is inhibited by diets containing Minari extract at various concentrations, based on measurements of the 8-OH deoxyguanosine level of DNA in the lung tissue of mice which have been treated with carcinogenic urethane. Furthermore, the effects of preventing cancer and cancer metastasis provided by the Minari extract of the present invention can be confirmed by examining whether or not diets containing Minari extract at various concentrations obstructs the occurrence of lung cancer in mice which have been treated with NNK, which is a potential carcinogen in cigarettes.

Furthermore, the effects of preventing cancer and cancer metastasis provided by the Minari extract of the present invention can be confirmed by examining to what extent the expression level of PCNA (proliferative cell nuclear antigen) in the lung tissue of mice which have been treated with NNK, which is a potential carcinogen in cigarettes, is suppressed by diets containing Minari extract at various concentrations.

Hereinafter, the present invention will be described by way of examples.

EXAMPLE 1

Effective Inhibition of Urethane Activity by Minari Extract (Step 1: Lung Cancer Prevention)

A/J mice were divided in three groups. Through a single gavage, urethane was administered to each group at 10,000, 20,000, and 40,000 times (125, 250, and 500 mg/kg b.w.) the human urethane exposure level.

Next, each group was further divided into two experimental groups: one of the groups (Minari-treated group) was allowed to take, ad lib., a feed to which dried Minari extract was added to 5% based on the feed for 4 months, while the other group (urethane control group) received a normal feed. The results are shown in FIG. 1. The incidence of lung cancer is significantly reduced in the Minari-treated groups ($p<0.05$).

(Step 2: Suppression of the Expression Level of the Cyclin D1 Oncogenic Gene)

Figure 2:
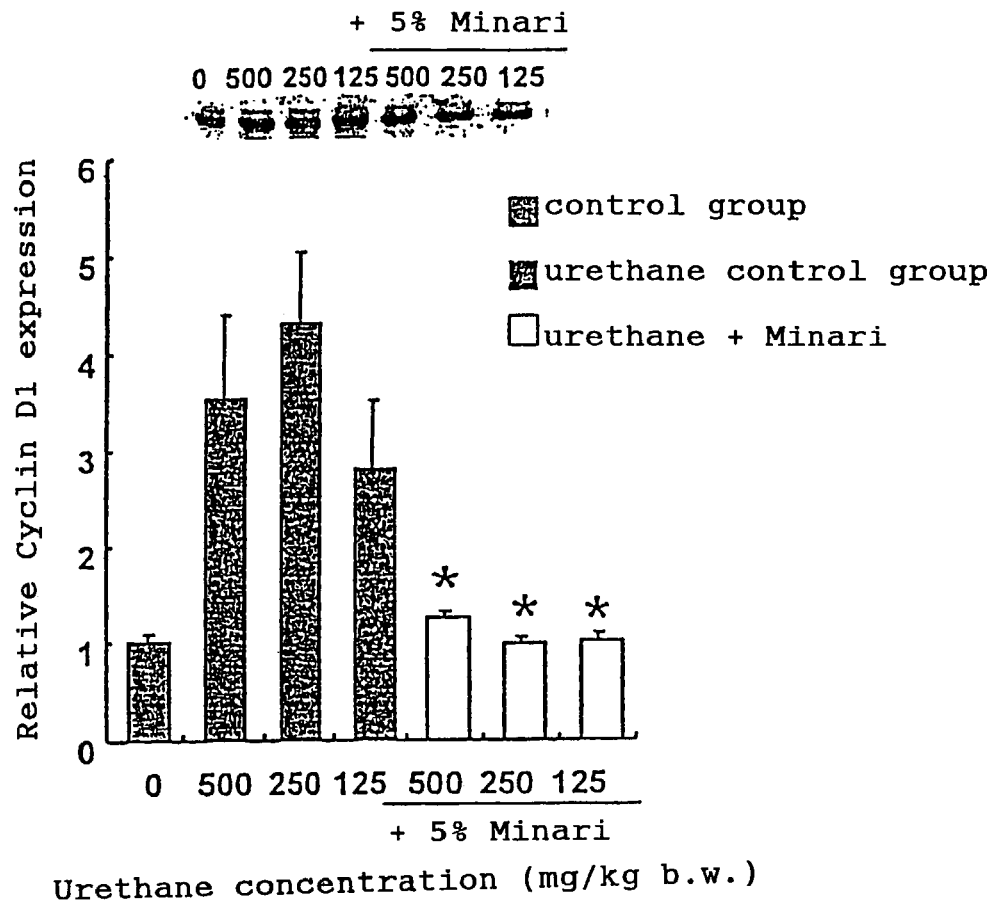
FIG. 2 demonstrates different expression levels of the cyclin D1 oncogene in lung tissue in three experimental groups of A/J mice, taken after 4 months following a single gavage of different amounts of urethane, as well as the suppressive effects of the Minari extract. Each of the three experimental groups, which respectively received a single administration of a 125, 250, or 500 mg/kg dose of urethane, was divided into two subgroups: one of the subgroups received a normal feed (urethane control group), while the other subgroup was allowed to take, ad lib., a feed to which Minari extract was added at a 5% concentration (w/w) for 4 months (urethane+Minari). After the experiment, the expression level of cyclin D1 was observed for each group.

A/J mice were divided into a control group and a urethane-receiving group. The urethane-receiving group was further divided into three groups, which respectively received urethane at doses of 125, 250, or 500 mg/kg. Each urethane-receiving group was further divided into two experimental groups: one of the groups (urethane-only-receiving group) received a normal feed, while the other group (urethane+Minari group) received a feed to which Minari extract was added at a 5% concentration for 4 months. The expression level of cyclin D1 was measured after completion of the experiment (The 91st Cancer Society, presentation article No. 5313: I. P. Lee, Pulmonary cyclin D1-induction by Fumonisin B1 in Female A/J mice, Apr. 15, 2000). The results are shown in FIG. 2. The urethane-only-receiving groups showed four times as high results as those of the Minari-treated groups.

(Step 3: Inhibition of PCNA Expression)

Figure 3:
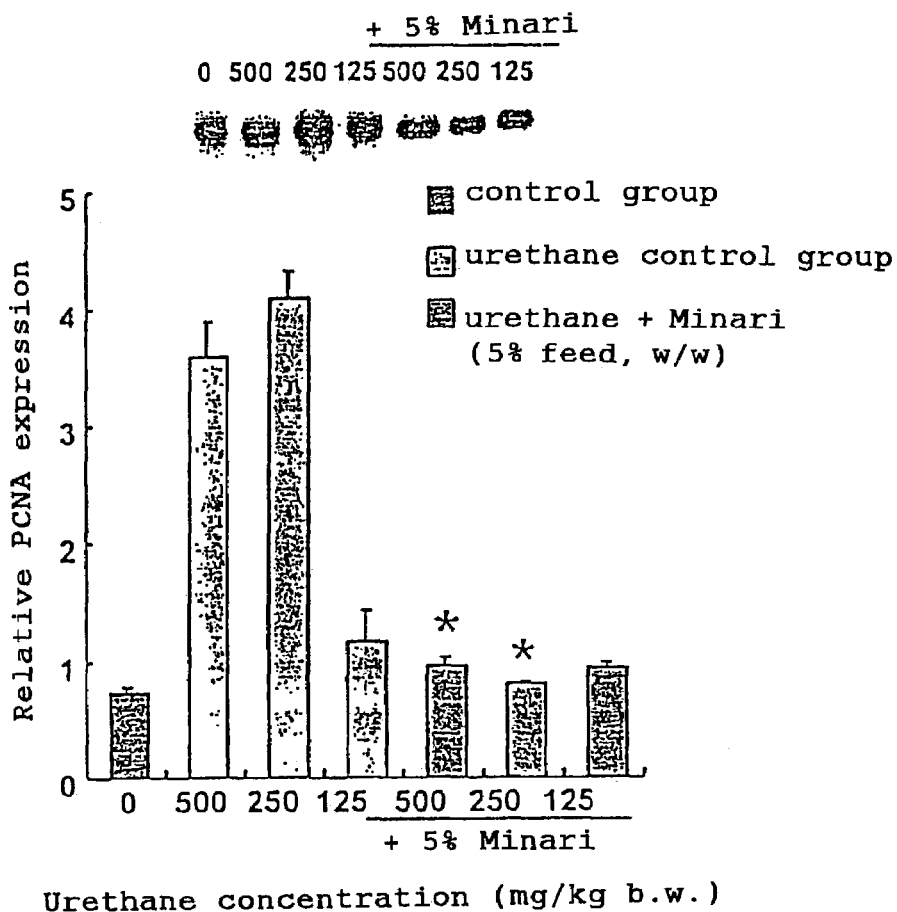
FIG. 3 demonstrates different expression levels of PCNA (proliferative cell nuclear antigen) of the S-phase of the cell cycle in lung tissue in three experimental groups of A/J mice, taken after 4 months following a single gavage of different amounts of urethane, as well as the suppressive effects of the Minari extract. Each of the three experimental groups, which respectively received a single administration of a 125, 250, or 500 mg/kg dose of urethane, was divided into two subgroups: one of the subgroups received a normal feed (urethane control group), while the other subgroup was allowed to take, ad lib., a feed to which Minari extract was added at a 5% concentration (w/w) for 4 months (urethane+Minari). After the experiment, the PCNA level in the lung tissue was observed for each group.

A/J mice were divided into a control group and a urethane-receiving group. The urethane-receiving group was further divided into three groups, which respectively received urethane at doses of 125, 250, or 500 mg/kg. Each urethane-receiving group was further divided into two experimental groups: one of the groups (urethane-only-receiving group) received a normal feed, while the other group (urethane+Minari group) received a feed to which Minari extract was added at a 5% concentration for 4 months. The PCNA (proliferative cell nuclear antigen) in the S-phase of the cell cycle was measured after completion of the experiment (The 91st Cancer Society, presentation article No. 5313: I. P. Lee, Pulmonary cyclin D1-induction by Fumonisin B1 in Female A/J mice, Apr. 15, 2000). The results are shown in FIG. 3. The PCNA level of the urethane-only-receiving groups had been increased to be four times as high as those of the urethane+Minari groups.

(Step 4: Suppression of DNA Damage as Indicated by 8-OH Deoxyguanosine Concentration)

Figure 4:
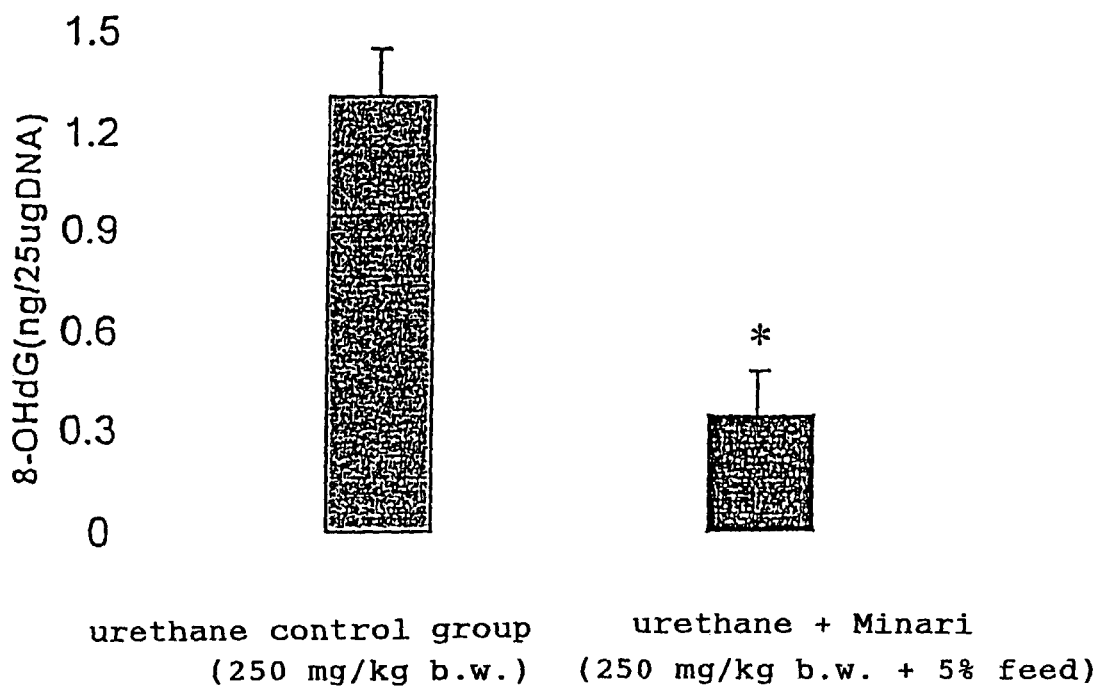
FIG. 4 demonstrates 8-OH deoxyguanosine levels of DNA isolated from lung tissue in three experimental groups of A/J mice, taken after 4 months following a single gavage of different amounts of urethane, as well as the suppressive effects of the Minari extract. Each of the three experimental groups, which respectively received a single administration of a 125 mg/kg (data not shown), 250 mg/kg, or 500 mg/kg (data not shown) dose of urethane, was divided into two subgroups: one of the subgroups received a normal feed (urethane control group), while the other subgroup was allowed to take, ad lib., a feed to which Minari extract was added at a 5% concentration (w/w) for 4 months (urethane+Minari). After the experiment, the 8-OH deoxyguanosine level of DNA isolated from the lung tissue was observed for each group.

A/J mice were divided into a control group and a urethane-receiving group. The urethane-receiving group was further divided into three groups, which respectively received urethane at doses of 125, 250, or 500 mg/kg. Each urethane-receiving group was further divided into two experimental groups: one of the groups (urethane-only-receiving group) received a normal feed, while the other group (urethane+Minari group) received a feed to which Minari extract was added at a 5% concentration for 4 months. The 8-OH deoxyguanosine concentration was measured after completion of the experiment. The results are shown in FIG. 4. The 8-OH deoxyguanosine concentration in the Minari-treated groups had been significantly reduced relative to those of the urethane-only-treated groups.

EXAMPLE 2

Minari Extract which Effectively Suppresses NNK Activation and Prevents Cancer (Step 1: Obstruction of Occurrence of Lung Cancer)

NNK, a potential carcinogen in cigarette smoke, was administered to a total of four groups of A/J mice: an NNK-only-receiving (+normal feed) group; and NNK+Minari-added-feed-receiving groups (1.25, 2.5 or 5% (w/w)) Such a dose of NNK corresponds to an amount equivalent to smoking a package of cigarettes for 100 years or more (Djordijevic, M. V. et al., Comparison of selected components in the mainstream smoke of the leading U.S. and Japanese cigarettes. In: Proceedings of the CORESTA smoke and Technology Meeting, pp. 200-217, Nov. 3-8, 1996). Four months later, the lung cancer multiplicity in the A/J mice was measured.

Figure 5:
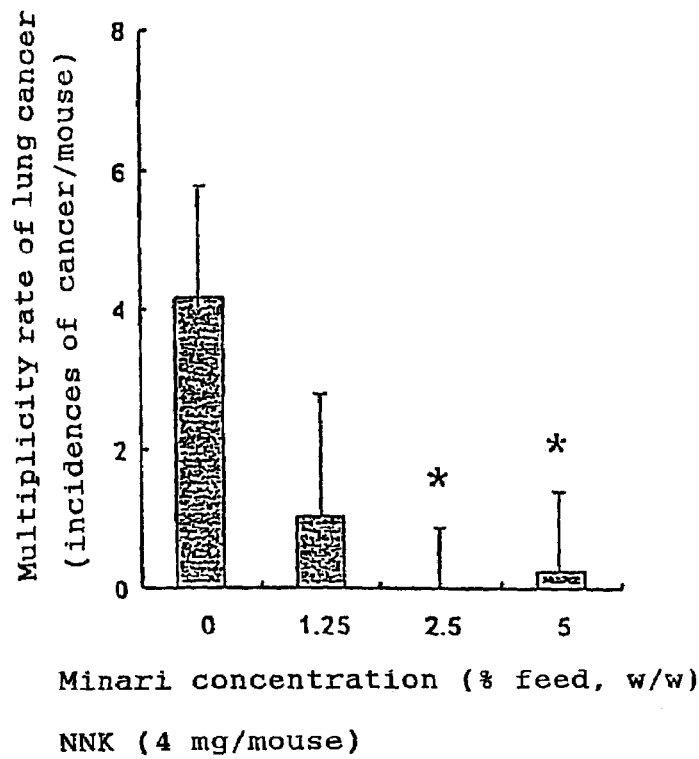
FIG. 5 demonstrates different levels of lung cancer multiplicity induced in four experimental groups of A/J mice, taken after 4 months following a single intraperitoneal administration of NNK[{(4-N-methyl-N-nitrosoamino)-1-(3-pyridyl)-1-buta none}], which is a potential carcinogen in cigarette smoke, as well as the suppressive effects of the Minari extract. The four experimental groups were: an NNK control group and three groups (receiving 4 mg of NNK) which were allowed to take, ad lib., Minari at three different doses (i.e., feed to which Minari was added at 1.25, 2.5, or 5% (w/w)).

The results indicate, as shown in FIG. 5, a significantly lower cancer incidence in the groups receiving pulverized Minari extract at 2.5% or 5% ($p<0.05$).

(Step 2: Suppression of the Cyclin D1 Oncogene)

Figure 6:
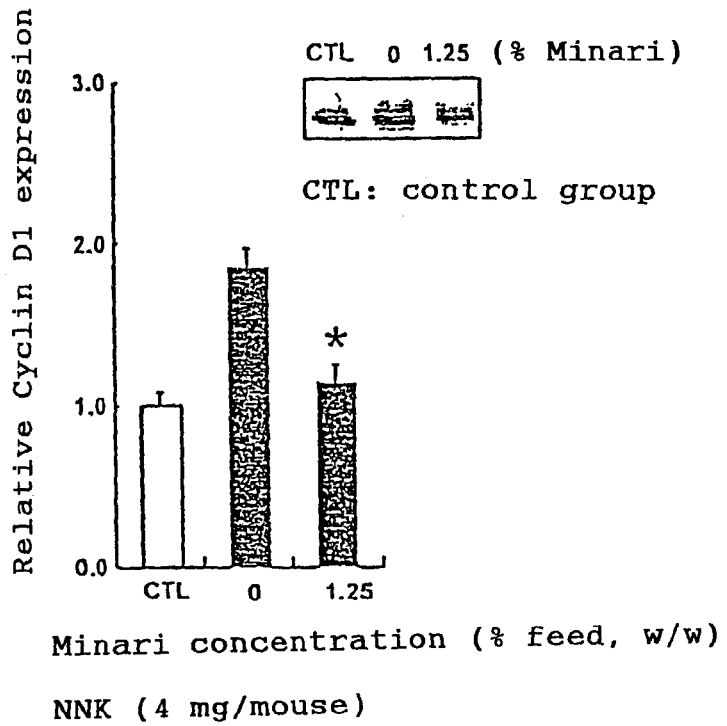
FIG. 6 demonstrates expression levels of the cyclin D1 oncogene in lung tissue in three groups: a control group to which water was intraperitoneally administered and which was thereafter allowed to take, ad lib., a normal feed (CTL) for 4 months; a group receiving a single intraperitoneal administration of NNK (4 mg) and thereafter allowed to take, ad lib., a normal feed for 4 months (shown as 0 in the figure); and a group receiving a single intraperitoneal administration of NNK (4 mg) and thereafter allowed to take, ad lib., a feed to which Minari extract was added (1.25%, w/w) for 4 months.

A/J mice were divided into three experimental groups: a single intraperitoneal water administration-receiving (+normal feed) group; a single intraperitoneal NNK (4 mg) administration-receiving (+normal feed) group; and a single intraperitoneal NNK administration-receiving (+feed to which Minari extract is added at a concentration of 1.25%) group. Four months later, the expression level of the cyclin D1 oncogene in each experimental group was measured. The results indicate, as shown in FIG. 6, that the expression level of cyclin D1, an oncogene, had been reduced to a half or less of that of an NNK control group ($p<0.05$). From this, it was indicated that the Minari extract significantly inhibits NNK activity with respect to the expression of cyclin D1.

(Step 3: Inhibition of PCNA Expression)

Figure 7:
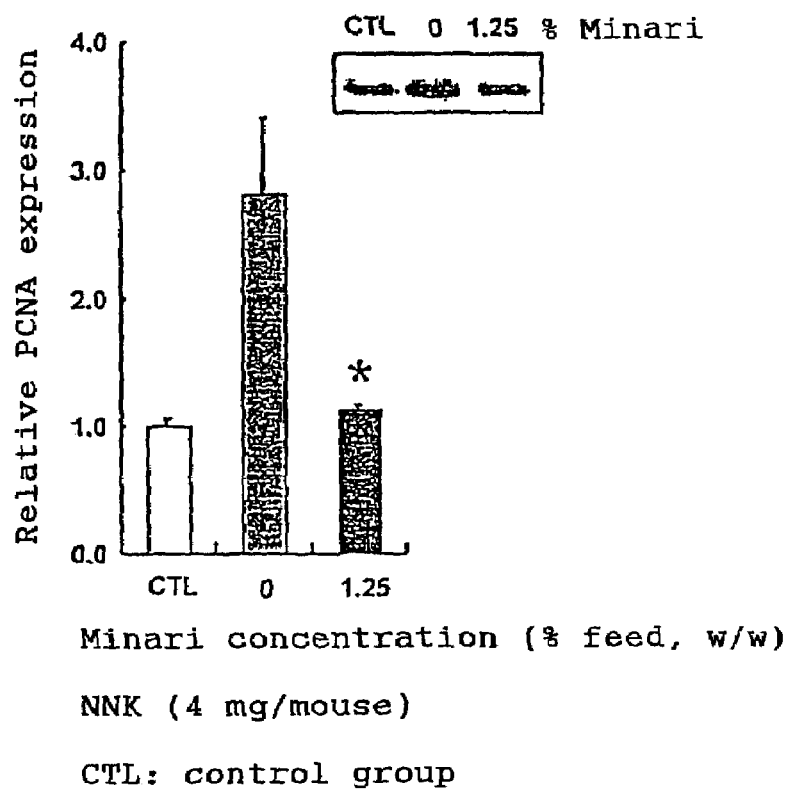
FIG. 7 demonstrates different expression levels of PCNA (proliferative cell nuclear antigen) of the S-phase of the cell cycle in lung tissue in three experimental groups: a control group (water); an NNK control group; and a group receiving NNK-Minari (1.25%, w/w), as well as the suppressive effects of the Minari extract. The NNK group received a single administration of 4 mg of NNK. The group receiving NNK-Minari received a single administration of NNK and thereafter a feed to which Minari extract was added at a 1.25% (w/w) concentration. The other group received a normal feed. All the groups were allowed take, ad lib., their feeds for 4 months. After the experiment, the PCNA level in the lung tissue was observed for each group.

A/J mice were divided into three experimental groups: a single intraperitoneal water administration-receiving (+normal feed) group; a single intraperitoneal NNK (4 mg) administration-receiving (+normal feed) group; and a single intraperitoneal NNK administration-receiving (+feed to which Minari extract is added at a concentration of 1.25%) group. Four months later, the expression level of PCNA in each experimental group was measured. The results indicate, as shown in FIG. 7, that the expression level of PCNA had significantly increased in the NNK-treated group, as compared to the water-only-receiving group. On the other hand, the PCNA expression level was significantly inhibited in the group which received Minari treatment (1.25% in the feed, w/w) in addition to NNK administration, as compared to the water-receiving group ($p<0.05$).

Industrial Applicability

The inventor has confirmed that Minari extract can obstruct lung cancer induced by urethane which is present in alcoholic beverages and carcinogenic foods or by NNK[{(4-N-methyl-N-nitrosoamino)-1-(3-pyridyl)-1-buta none}] present in cigarette smoke, thereby accomplishing the present invention. The possible mechanism of cancer prevention by Minari extract is presumably via obstruction of the activation of precarcinogens into more active carcinogens, and via removal of free radicals, which are present in cigarette smoke and alcoholic beverages, by a number of free radical scavengers within Minari extract. Furthermore, an objective of the present invention is to prevent, typically, the occurrence of lung cancer and consequent cancer metastasis due to carcinogens targeting the lungs, by the use of a dietary ingredient of Minari extract containing the very effective chemical preventive substance.

As specifically described in the examples, Minari extract potentially prevents lung cancer or other cancer induced by carcinogens present in fermented foods, alcoholic beverages, or cigarette smoke, and is very important to the medical industry.

The invention claimed is:

1. A method of reducing the incidence of lung cancer comprising administering to an individual an effective amount of a Minari extract, which is prepared by extracting a Korean native dol-minari of *Oenanthe javanica* plant in hot water, and which comprises a component which reduces expression of cyclin D1.

2. A method according to claim 1, wherein the lung cancer is cancerwhich can be induced by urethane or NNK [{4-N-methyl-N-nitrosoamino)-1-(3-pyridyl)-1-butanone}].

3. A method of reducing the incidence of lung cancer comprising administering to an individual an effective amount of a composition comprising a pharmaceutically acceptable carrier and a Minari extract, wherein the Minari extract is prepared by extracting a Korean native dol-minari of *Oenanthe* javanica plant in hot water.

4. A method according to claim 3, wherein said composition is in a form selected from the group consisting of powder, liquid, tablets, capsules, and pellets.

5. A method of reducing the incidence of lung cancer comprising administering to an individual an effective amount of a Minari extract comprising a component which is useful as a therapeutic agent for treating cancer in a specimen, wherein the cancer is lung cancer, wherein the cancer is cancer induced by urethane or NNK, and wherein the extract is prepared by extracting a Korean native dol-minari of *Oenanthe* javanica plant in hot water.

6. A method of reducing the incidence of lung cancer comprising administering to an individual an effective amount of a Minari extract prepared by extracting plant material of a Korean native dol-minari of *Oenanthe* javanica plant in hot water, comprising components which reduce expression of cyclin D1; reduce expression of proliferative cell nuclear antigen (PCNA); reduce NNK activation and thereby reduce lung cancer multiplicity; and reduce the expression level of PCNA.

* * * * *